United States Patent
Berry et al.

(10) Patent No.: US 11,369,279 B2
(45) Date of Patent: Jun. 28, 2022

(54) OFF-RESONANCE CORRECTION FOR PSEUDO-CONTINUOUS ARTERIAL SPIN LABELING

(71) Applicant: Isis Innovation Limited, Oxford (GB)

(72) Inventors: Eleanor Berry, Oxford (GB); Thomas Okell, Oxford (GB); Peter Jezzard, Oxford (GB)

(73) Assignee: OXFORD UNIVERSITY INNOVATION LIMITED, Oxford (GB)

(*) Notice: Subject to any disclaimer, the term of this patent is extended or adjusted under 35 U.S.C. 154(b) by 1628 days.

(21) Appl. No.: 14/999,198

(22) Filed: Apr. 8, 2016

(65) Prior Publication Data
US 2016/0296126 A1  Oct. 13, 2016

Related U.S. Application Data

(60) Provisional application No. 62/178,418, filed on Apr. 9, 2015.

(51) Int. Cl.
| | | |
|---|---|---|
| *A61B 5/026* | (2006.01) | |
| *A61B 5/00* | (2006.01) | |
| *G01R 33/563* | (2006.01) | |
| *G01R 33/483* | (2006.01) | |
| *G01R 33/565* | (2006.01) | |

(52) U.S. Cl.
CPC .......... *A61B 5/0263* (2013.01); *A61B 5/489* (2013.01); *A61B 5/7257* (2013.01); *G01R 33/4838* (2013.01); *G01R 33/56366* (2013.01); *A61B 2576/026* (2013.01); *G01R 33/5635* (2013.01); *G01R 33/56518* (2013.01)

(58) Field of Classification Search
CPC . A61B 2576/026; A61B 5/0263; A61B 5/489; A61B 5/7257; G01R 33/4838; G01R 33/5635; G01R 33/56366; G01R 33/56518
See application file for complete search history.

(56) References Cited

U.S. PATENT DOCUMENTS

| | | | |
|---|---|---|---|
| 2010/0240983 A1 | 9/2010 | Jung et al. | |
| 2012/0271157 A1* | 10/2012 | Wong | A61B 5/0042 600/419 |
| 2013/0231554 A1* | 9/2013 | Jung | G01R 33/56366 600/419 |

(Continued)

OTHER PUBLICATIONS

Wong (Vessel-Encoded Arterial Spin-labeling Using Pseudocontinuous Tagging; Magnetic Resonance in Medicine 58:1086-1091; 2007).*

(Continued)

*Primary Examiner* — Shahdeep Mohammed
(74) *Attorney, Agent, or Firm* — Thomas|Horstemeyer, LLP

(57) ABSTRACT

Systems and methods are provided to incorporate an off-resonance correction into the pulse labeling train of PCASL/VEPCASL. In one or more aspects, the systems and methods are based on a method for generating an encoding scheme for any number and arrangement of blood vessels. The off-resonance correction can be incorporated into the generation of optimized encodings to acquire arterial spin labeling (ASL) data, such as PCASL and VEPCASL data.

21 Claims, 7 Drawing Sheets
(6 of 7 Drawing Sheet(s) Filed in Color)

(56) References Cited

U.S. PATENT DOCUMENTS

| | | | | |
|---|---|---|---|---|
| 2015/0276909 A1* | 10/2015 | Kawaji | ............... | G01R 33/5673 600/413 |
| 2015/0305645 A1* | 10/2015 | Ouyang | ............ | G01R 33/56366 600/419 |

OTHER PUBLICATIONS

Berry et al. ("An optimized encoding scheme for planning vessel-encoded pseudocontinuous arterial spin labeling"; published online Oct. 2014 in Willey Online Library (Wileyonlinelibrary.com) (Year: 2014).*

Luh et al. ("pseudo-continuous arterial spin labeling at 7T for human brain: estimation and correction for off-resonance effects using a prescan"; Magnetic Resonance in Medicine 69:402-410, 2013).*

Shin et al. ("pseudocontinuous arterial spin labeling with optimized tagging efficiency"; Magnetic Resonance in Medicine 68:1135-1144m, 2012).*

E. S. K. Berry, P. Jezzard, and T. W. Okell, "An optimized encoding scheme for planning vessel-encoded pseudocontinuous arterial spin labeling," Magn Reson Med, vol. 74, pp. 1248-1256, Nov. 2015.

E. S. K. Berry, P. Jezzard, and T. W. Okell, "An off-resonance correction method for vessel-encoded pseudo-continuous arterial spin labeling using the optimized encoding scheme," in Proceedings 23rd Scientific Meeting, ISMRM, (Toronto, Canada), p. 272, May 2015.

E. S. K. Berry, P. Jezzard, and T. W. Okell, "Off-resonance corrections for unipolar vessel-encoded pseudo-continuous arterial spin labelling," in Proceedings 23rd Postgraduate Symposium, British Chapter of the ISMRM, (Cardiff, UK), p. O7, Apr. 2014.

Wong EC. Vessel-encoded arterial spin-labeling using pseudocontinuous tagging. Magn Reson Med 2007;58:1086-1091.

Wu WC, Jiang SF, Yang SC, Lien SH. Pseudocontinuous arterial spin labelling perfusion magnetic resonance imaging—a normative study of reproducibility in the human brain. Neuroimage 2011;56:1244-50.

Jahanian H, Noll DC, Hernandez-Garcia L. B0 field inhomogeneity considerations in pseudo-continuous arterial spin labeling (pCASL): effects on tagging efficiency and correction strategy. NMR Biomed 2011;24:1202-9.

Luh WM, Talagala SL, Li TQ, Bandettini PA. Pseudo-continuous arterial spin labelling at 7 T for human brain: estimation and correction for off-resonance effects using a Prescan. Magn Reson Med 2013;69:402-10.

D. D. Shin, T. T. Liu, E. C. Wong, A. Shankaranarayanan, and Y. Jung, "Pseudocontinuous arterial spin labeling with optimized tagging efficiency," Magn Reson Med, vol. 68, pp. 1135-1144, Oct. 2012.

* cited by examiner

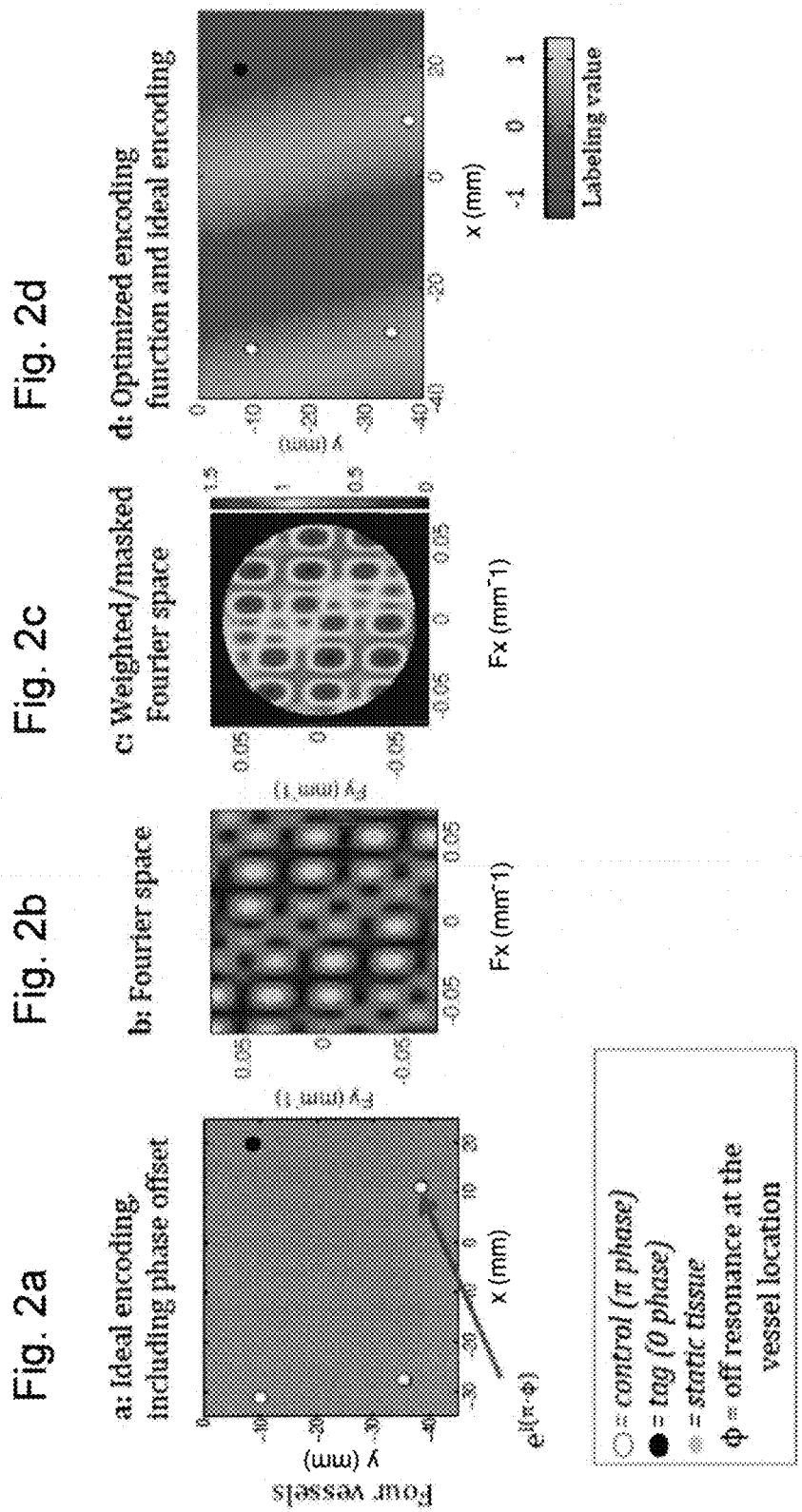

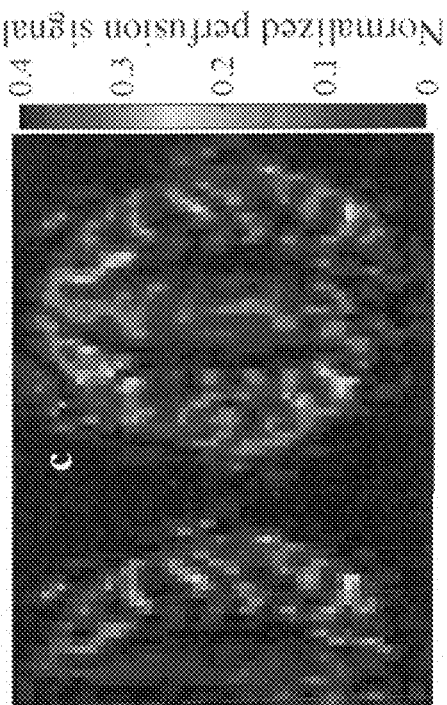
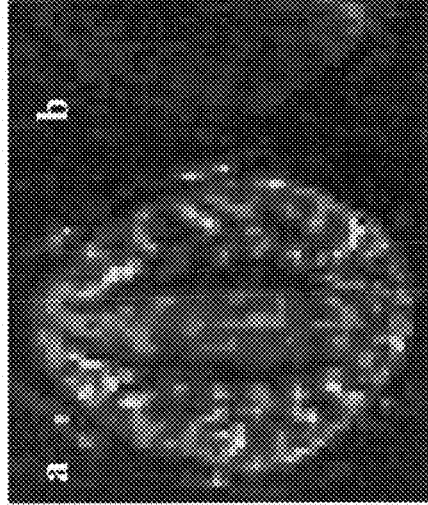
Fig. 6a Fig. 6b Fig. 6c
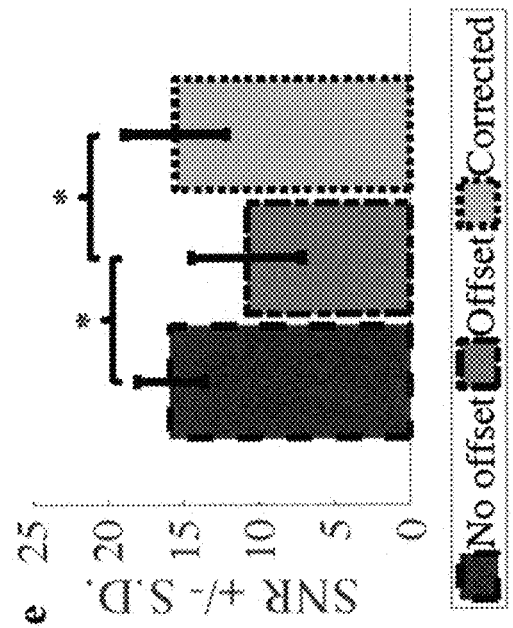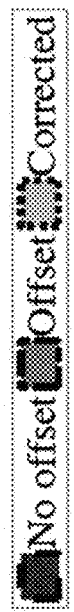
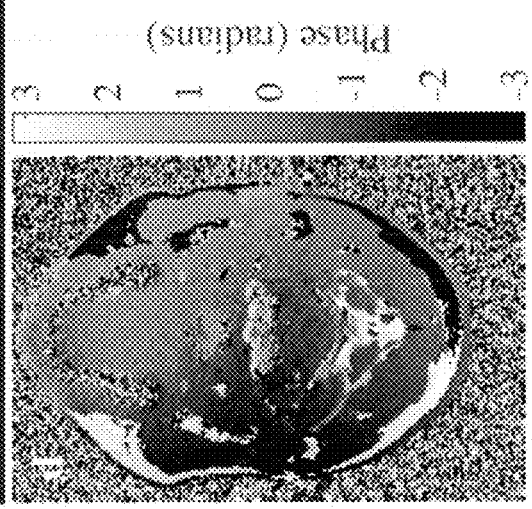
Fig. 6e
Fig. 6d Fig. 7a  Fig. 7b  Fig. 7c
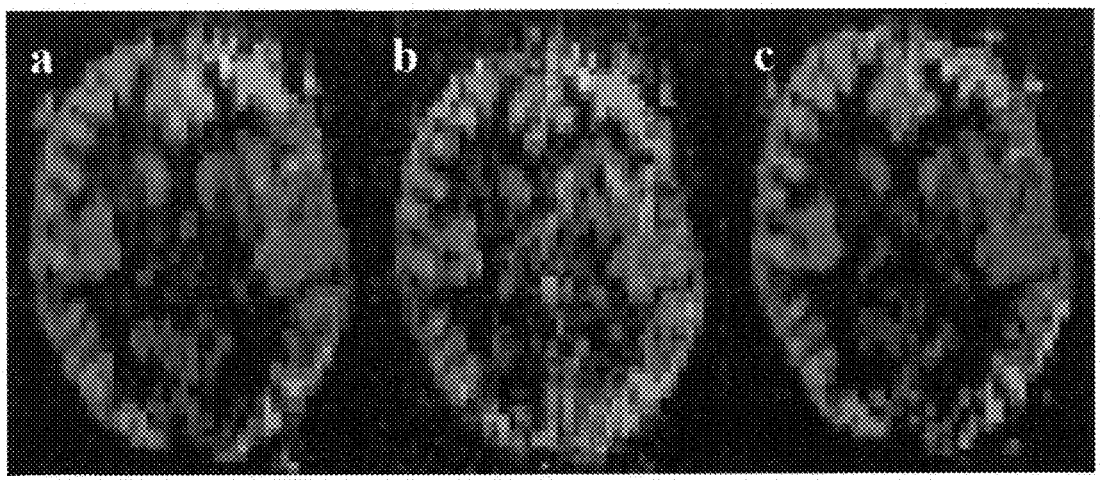
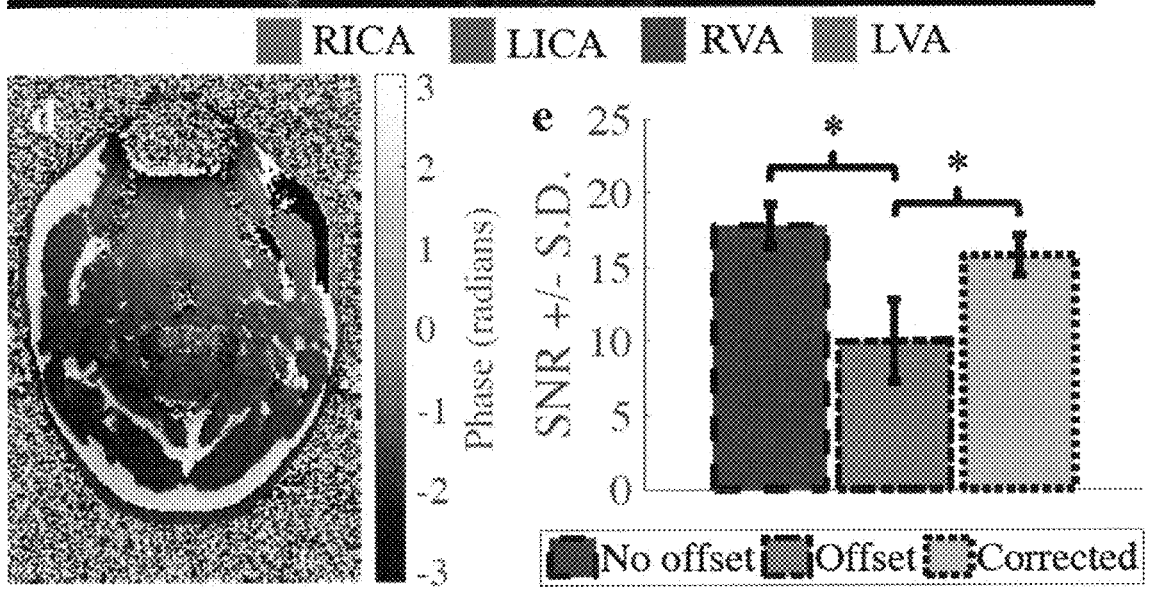
Fig. 7d  Fig. 7e

OFF-RESONANCE CORRECTION FOR PSEUDO-CONTINUOUS ARTERIAL SPIN LABELING

CROSS-REFERENCE TO RELATED DOCUMENTS

This application claims priority to, and the benefit of U.S. Provisional Patent Application entitled, "OFF-RESONANCE CORRECTION FOR PSEUDO-CONTINUOUS ARTERIAL SPIN LABELING", having Ser. No. 62/178,418, filed on Apr. 9, 2015, which is incorporated by reference in its entirety.

TECHNICAL FIELD

The present disclosure generally relates to medical imaging and more particularly, relates to systems and methods for providing clinicians with blood flow rate information to help make diagnostic, prognostic or therapeutic decisions.

BACKGROUND

Angiographic methods, which generate images of blood vessels, are of great importance in the assessment of vascular diseases, such as atherosclerosis and arteriovenous malformation. They can provide information on vessel morphology and function, which aids clinicians with diagnosis, prognosis and treatment planning in these patients. Likewise, the measurement of perfusion can provide information about the condition of tissue in the brain and other organs.

There are a variety of invasive and non-invasive methods for acquiring angiographic and perfusion information in the brain. Pseudo-continuous arterial spin labeling (PCASL) is a non-invasive magnetic resonance imaging (MRI) method used for obtaining this information. It is also possible to use vessel-encoded PCASL (VEPCASL) to acquire vessel-selective angiograms [1] and vascular territory maps. These allow collateral circulation in the brain to be visualized, and a knowledge of collateral circulation can help the understanding and potential treatment of stroke and other cerebrovascular diseases [2, 3]. The gold standard for acquiring vessel-selective information is X-ray digital subtraction angiography. X-ray digital subtraction angiography is an invasive method, requiring both the insertion of a catheter to administer a contrast agent, carrying an associated risk of stroke or transient ischemic attack [4], and the use of ionizing radiation [5].

PCASL has been shown to have higher signal-to-noise ratio (SNR) than pulsed arterial spin labeling [6], and VEPCASL yields an SNR comparable to that of standard PCASL[7]. Additionally, compared with other vessel-selective methods, VEPCASL is capable of labeling vessels that are closer together [8]. With VEPCASL vessel selectivity is achieved by varying the labeling efficiency periodically across the plane in which vessels are tagged. The spatial frequency and phase of this "encoding function" can be adjusted to allow different combinations of vessels to be tagged and controlled for any given measurement [9]. There are a number of ways to choose the encoding functions that will best label/control the vessels of interest. An automated method generating SNR optimized encodings for any number and arrangement of vessels has now been published [10].

We have found that off-resonance in the labeling plane during PCASL, and likewise during VEPCASL, can occur leading to a reduction in labeling efficiency. Such a reduction can result in a loss of SNR in the resulting perfusion images or angiograms and errors in quantitative estimates of blood flow rates, discussed in more detail below.

Some techniques have been proposed to correct for such off-resonance effects, either during labeling or by trying to calculate the true labeling efficiency during image analysis [11, 12]. However, most are restricted to correcting limited types of off-resonance and/or are applicable to only a small number of arteries. Some of these methods also require additional PCASL scans, which can add considerably to the total scan time and result in a loss in SNR, and/or more complex methods requiring manual intervention to calculate the corrections needed.

SUMMARY

As a result of the aforementioned problems, we developed the systems and methods, described herein, to incorporate, in an aspect, an off-resonance correction into the pulse labeling train of arterial spin labeling (ASL), for example PCASL/VEPCASL. In one or more aspects, our systems and methods are directed to a method for generating an Optimized Encoding Scheme (OES) for any number and arrangement of vessels [10]; the off-resonance correction can be incorporated into the generation of the optimized encodings.

Provided herein, in various aspects, are systems and methods to correct for the effects of off-resonance (magnetic field inhomogeneity) present in MRI, in particular present in the labeling plane during arterial spin labeling (ASL). The present systems and methods provide a relatively simple framework to implement and are applicable to any pattern of off-resonance and any number of vessels. The technique is suitable for use with both VEPCASL and the more widely used PCASL. In one or more aspects an Optimized Encoding Scheme (OES) is utilized incorporating an off-resonance correction. The optimized encodings incorporating the off-resonance correction do not add any extra time onto the scan and there is little or no loss in SNR. Any additional phase information needed can be provided by a field map acquired in less than a minute without further calculation.

In an embodiment, we present a method that incorporates a correction for off-resonance into an encoding scheme for multiple vessels prior to the acquisition of arterial spin labeling (ASL) data, for example PCASL or VEPCASL data or both. In an embodiment, we provide a system and method utilizing an encoding scheme along with phase information from a field map to mitigate the effects of off-resonance at the vessel locations, i.e. we account for phase offsets due to off-resonance. In one or more aspects, it can be a rapid optimized encoding scheme (OES) that automates the choice of SNR-efficient encodings, regardless of the number or arrangement of vessels [10] and regardless of the phase offsets present at the vessel locations. An example of a suitable encoding scheme is provided in Berry et al. 2014 (Berry, E. S. K., Jezzard, P. and Okell, T. W. (2015), An Optimized Encoding Scheme for Planning Vessel-Encoded Pseudocontinuous Arterial Spin Labeling. Magn Reson Med, 74: 1248-1256. doi: 10.1002/mrm.25508), which is incorporated by reference as if fully set forth herein.

Briefly described, one embodiment, among others, is a method for off-resonance correction prior to the acquisition of arterial spin labeling (ASL) data, comprising:
  A. Providing a medical imaging device;
  B. Positioning a subject in association with the medical imaging device;

C. Acquiring information about the location of blood vessels of interest in the subject and phase offsets at the location of the blood vessels;

D. Determining the encodings to apply to a labeling plane to encode the blood vessels of interest whilst accounting for the phase offset at each blood vessel location for which information is acquired; and E. Acquiring arterial spin labeling (ASL) data, which includes the blood vessels of interest in the subject, using the determined encodings and using the medical imaging device.

The method can be computer implemented or implemented in a processing device.

In an embodiment, among others, a system is provided for off-resonance correction prior to the acquisition of arterial spin labeling (ASL) data comprising: at least one medical imaging device configured for positioning a subject in association with the medical imaging device; at least one computing device in data communication with the medical imaging device; and an application executable in the at least one computing device, the application comprising logic that:

A. Acquires information about the location of blood vessels of interest in the subject and phase offsets at the location of the blood vessels;

B. Determines the encodings to apply to a labeling plane to encode the blood vessels of interest whilst accounting for the phase offset at each blood vessel location for which information is acquired; and C. Acquires arterial spin labeling (ASL) data, which includes the blood vessels of interest in the subject, using the determined encodings and using the medical imaging device.

In an embodiment, among others, a non-transitory computer-readable medium is provided employing a program executable in at least one computing device, comprising code that:

A. Acquires information about the location of blood vessels of interest in a subject and phase offsets at the location of the blood vessels of interest from a medical imaging device configured for positioning the subject in association with the medical imaging device;

B. Determines the encodings to apply to a labeling plane to encode the blood vessels of interest whilst accounting for the phase offset at each vessel location for which information is acquired; and C. Acquires arterial spin labeling (ASL) data, which includes the blood vessels of interest in the subject, using the determined encodings and using the medical imaging device.

In any one or more aspects, the method, system and/or non-transitory computer-readable medium can further include: determining the encodings by taking a Fourier transform of an idealized "image" of the blood vessels, including phase offsets at the location of the blood vessels; up-weighting the resulting Fourier transform of the image to up-weight lower spatial frequencies in a Fourier space (or transform domain); and finding a maximum intensity point in the up-weighted Fourier space. In one or more aspects, the arterial spin labeling (ASL) data acquired can include PCASL or VEPCASL data or both. Acquiring information about the location of the blood vessels of interest and phase offsets at the location of the blood vessels can involve a field map of the desired labeling plane, can include input of the vessel locations, and/or include creating an encoding matrix. The blood vessels can be placed in the matrix at positions corresponding to their physical Cartesian coordinates within a labeling plane.

In any one or more aspects, the method can further include zero-padding the "image" and/or up-weighting the resulting Fourier transform can include masking spatial frequencies within the Fourier space. Before the maximum intensity point is found, the absolute value of the Fourier transform can be taken and normalized to its maximum value and then the up-weighting can be done. The process can be repeated for each cycle of the encoding scheme, and the data can include perfusion data or static/dynamic angiography data.

Other systems, methods, features, and advantages of the present disclosure will be, or will become, apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views. These drawings exemplify the present disclosure using VEPCASL perfusion data, although PCASL and/or dynamic angiographic data could be used here.

FIGS. 2a-2d depict an embodiment of the present method for four vessels, representative of the main brain-feeding vessels in the neck. FIG. 2a depicts "Images" of ideally encoded vessels of interest; static tissue is set to zero. FIG. 2b depicts Fourier transforms of the zero-padded "images." FIG. 2c depicts weighted and masked Fourier spaces. The maximum intensity points are indicated by arrows. FIG. 2d depicts optimized encoding functions overlaid onto the ideal encodings.

FIG. 5a depicts anterior-posterior (AP) encoding without any offset applied. Anterior arteries are labeled, posterior controlled. FIG. 5b depicts a field map showing a linear shim offset in the labeling plane. FIG. 5c depicts AP encoding in the presence of the offset. The encoding has shifted from the desired vessels. FIG. 5d depicts AP encoding corrected for the applied phase offset, desired vessels are labeled/controlled.

FIGS. 6a-6e depict images of the perfusion signal in the brain for the main brain-feeding arteries of a representative subject and the mean SNR of this perfusion signal across a group of subjects. The perfusion signal in a single slice of the brain following PCASL is shown for no offsets in the labelling plane (FIG. 6a), offsets, un-corrected in the encoding (FIG. 6b), and an offset corrected encoding (FIG. 6c). The perfusion signal in the right hemisphere has been recovered versus FIG. 6e. FIG. 6d depicts field map of the labeling plane after shim adjustments to generate phase offsets. FIG. 6e depicts Mean SNR±standard deviation of the perfusion signal. No offset=15.8±2.3, offset=10.8±3.7, corrected=15.5±3.4.

FIGS. 7a-7e depict images of the perfusion signal in the brain for the main brain-feeding arteries of a representative subject and the mean SNR of this perfusion signal across a group of subjects. The vascular territories of the main brain feeding arteries following VEPCASL is shown for no offsets in the labeling plane (FIG. 7a), offsets, un-corrected in the encoding (FIG. 7b) and offsets corrected in the encoding (FIG. 7c). Perfusion signal has been assigned to the vascular territories similarly to the case where no offsets are present in the labeling plane. FIG. 7d depicts a field map of the labeling plane after shim adjustments to generate phase offsets. FIG. 7e depicts Mean SNR±standard deviation of the vascular territory signal. No offset=17.8±1.4, offset=10.0±2.8, corrected=15.8±1.4.

DETAILED DESCRIPTION

Figures 1A, 1B:
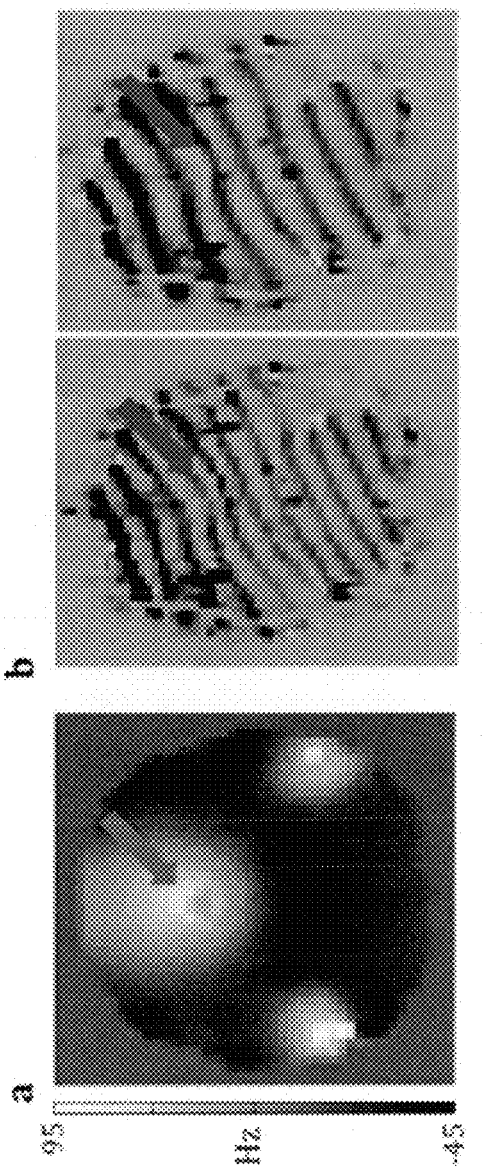
FIG. 1a illustrates a field map above the circle of Willis.
FIG. 1b illustrates two different encoding functions in a labeling plane above the circle of Willis. The largest field offsets (red arrow) cause the greatest shifts in the VEPCASL encoding functions (blue arrows).

Having summarized various aspects of the present disclosure, reference will now be made in detail to the various embodiments of the present systems and methods for an off-resonance correction for pseudo-continuous arterial spin labeling. Although particular embodiments are described, those embodiments are mere exemplary implementations of the system and method. One skilled in the art will recognize other embodiments are possible. All such embodiments are intended to fall within the scope of this disclosure. Moreover, all references cited herein are intended to be and are hereby incorporated by reference into this disclosure as if fully set forth herein. While the disclosure will now be described in reference to the above drawings, there is no intent to limit it to the embodiment or embodiments disclosed herein. On the contrary, the intent is to cover all alternatives, modifications and equivalents included within the spirit and scope of the disclosure.

Discussion Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for.

It is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in a different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Ratios, concentrations, amounts, and other numerical data may be expressed in a range format. It is to be understood that such a range format is used for convenience and brevity, and should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1% to about 5%, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figure of the numerical value. In addition, the phrase "about 'x' to 'y'" includes "about 'x' to about 'y'".

Description

Arterial spin labeling, for example in the brain, is a widely used technique that magnetically labels the blood travelling into the brain and, following the subtraction of an image containing unlabeled blood, leads to either angiographic or perfusion information in the brain. PCASL is a particular version of arterial spin labeling and VEPCASL builds on this by allowing vessels of interest to be separately labeled, or encoded, yielding vessel specific information (e.g. maps of the territories fed by specific vessels in the brain). These encodings can be visualized as spatial frequencies across the plane in which the blood is labeled, with the peaks and troughs of the function corresponding to control and label locations respectively. The periodic nature of the encoding function is a result of the particular magnetic field gradients applied to the labeling plane during the VEPCASL labeling pulse train.

The systems and methods described herein take into account off-resonance present in the labeling plane due to magnetic field inhomogeneities. In the case of unipolar VEPCASL [13] phase offsets at the vessel locations, due to off-resonance, will shift the encodings (or spatial frequencies) and reduce the labeling efficiency at the vessel locations. For example, the nonlinear inhomogeneities resulting from air in the sinuses and ear canals can lead to distortions in the encoding functions (see FIGS. 1a and b). FIG. 1a illustrates a field map above the circle of Willis and FIG. 1b two different encoding functions in a labeling plane above the circle of Willis. The largest field offsets (red arrow) cause the greatest shifts in the VEPCASL encoding functions (blue arrows).

In one or more aspects, the present systems and methods take into account phase information from a field map of the labeling plane and use this to inform the choice of encoding. It is possible to specify the desired phase at a given vessel location (e.g., zero phase at a given location during the labeling in order to label a vessel there) and find the encodings that best achieve this. If the phase offset due to off-resonance at a vessel location is included at this stage then encodings can be chosen that cancel out these phase offsets and mitigate some of the loss in labeling efficiency.

The present systems and methods can be applied not only to VEPCASL but also to PCASL itself, a much more commonly used method. They work in the same way for PCASL as for VEPCASL—the only difference is that we are trying to label all of the vessels at once, rather than a specific subset of vessels.

Encoding Schemes

An encoding scheme specifies which arteries are tagged or controlled during a given VEPCASL or PCASL encoding cycle. The encoding matrix is the mathematical description of the encoding scheme from which the SNR efficiency can be derived according to Wong [9]. The signal within each voxel is described mathematically as:

$$y = A \cdot x \quad [1]$$

where, y is the vector of measured signal intensities for all encoding cycles, A is the encoding matrix, and x is the unknown vector describing the signal contributions from each vessel plus static tissue [9].

Ideal encoding matrices are those whose SNR efficiency is equal to one for all vessels [9], which requires that the arteries are perfectly tagged (−1) and controlled (+1) an equal number of times. An example ideal encoding matrix for four vessels in the neck, described by Okell et al. [1], is shown below. The columns describe (from left to right) the label/control state of the right internal carotid artery, left internal carotid artery, right vertebral artery, left vertebral artery, and static tissue, respectively, for each encoding (or row).

$$A = \begin{bmatrix} -1 & -1 & -1 & -1 & 1 \\ 1 & 1 & 1 & 1 & 1 \\ -1 & 1 & -1 & 1 & 1 \\ 1 & -1 & 1 & -1 & 1 \\ -1 & -1 & 1 & 1 & 1 \\ 1 & 1 & -1 & -1 & 1 \\ -1 & 1 & 1 & -1 & 1 \\ 1 & -1 & -1 & 1 & 1 \end{bmatrix}$$

The columns of this matrix come from a Hadamard matrix. An encoding matrix consisting of columns from a Hadamard matrix will always have an SNR efficiency of one [9]. The order of a Hadamard matrix must be 1, 2, or an order of 4. When the number of vessels of interest (plus static tissue) does not match the order of a possible Hadamard matrix, then ideal encodings can be composed of the columns of the Hadamard matrix closest in size to (but greater than) the number of vessels. Consequently, there may be more encodings than are strictly necessary to extract the information about all the vessels. However, these extra encodings give the overall encoding scheme the greatest SNR efficiency.

Off-Resonance Correction

Our off-resonance correction (ORC) systems and methods can automate the choice of the encoding function used to tag/control the arteries of interest in a given VEPCASL cycle, whilst compensating for phase offsets at the vessel locations. In an aspect, it relies on defining an ideal encoding scheme that includes the phase offsets at the vessel locations and finding real encodings that match these as closely as possible. In an embodiment, with reference to FIGS. 2a-2d, the systems and methods can be structured to include the following steps:

1. Constructing an "image" of the vessel locations (FIG. 2a). For example, each vessel can be represented by $e^{i\theta}$, where θ is the desired phase, including the subtraction of the phase offset due to magnetic field inhomogeneities at that vessel location. Zeros can represent static tissue.
2. Zero-padding the "image."
3. Taking a Fourier transform of the zero-padded "image" (FIG. 2b).
4. Weighting (for example, using Eq. 2) and masking the resulting Fourier space to up-weight lower spatial frequencies (FIG. 2c); the weighting can make the encodings more robust to subject motion.

5. Finding the maximum intensity point(s) in this weighted Fourier space (FIG. 2c).

The maximum intensity point(s) in the weighted Fourier space can provide the spatial frequency and phase of the optimized encoding function that includes the ORC (FIG. 2d). This process can be repeated for each cycle of the encoding scheme.

The algorithm can construct the "image" of the vessels following the manual input of the vessel locations. In an aspect, the vessels, represented by $e^{i\theta}$, are placed in a matrix of zeros, at positions corresponding to their physical Cartesian coordinates within the labeling plane. Zero-padding the image increases the resolution in Fourier space, allowing the optimal spatial frequency to be identified more precisely.

Up-weighting lower spatial frequencies while masking higher ones can make the method more robust to gross subject motion; if a chosen encoding function has a low spatial frequency, then should a subject move, the vessels of interest will remain close to the desired encoding. If the vessels of interest are close together, a higher spatial frequency can be required to efficiently differentiate them. However, if the spatial frequency is too high, even a small amount of movement could shift a vessel from a label to a control location, leading to considerable deviation from the desired encoding. In addition, at very high spatial frequencies, there may be considerable variation in inversion efficiency across the diameter of a vessel, thereby reducing the average inversion efficiency and causing further deviations from the expected encoding. The weighting function can be present to ensure the algorithm has a tendency to choose lower spatial frequencies where there is a range of possible encoding functions that give a good match to the desired encoding. Note that there is no lower limit on the choice of spatial frequency, since encoding functions with wavelengths much larger than the separation of the vessels cannot give a good match to the desired encoding and, therefore, will be excluded by the algorithm.

In one or more aspects, before the maximum intensity point is identified, the absolute value of the Fourier space can be taken, normalized to its maximum value, and then the weightings added. The weighting function can be based on the position of each point in the Fourier space. For example, for a given point at a distance f from the center of the Fourier space, the weighting w can be:

$$w = \left( \frac{1 - f/f_{max}}{2} \right) \quad [2]$$

where, $f_{max}$ is the maximum possible distance of any point from the center. The coordinates of the maximum intensity point in the normalized weighted and masked Fourier space give the spatial frequency and direction of the optimum encoding function, with phase extracted from the same point in the unnormalized, unweighted Fourier space. A linear weighting function is described here but other smooth, slowly varying weighting functions can yield similar results.

The radius of the Fourier space mask can be set so that the wavelengths of the chosen encoding functions are at least four times the maximum predicted subject motion. This can help to ensure that, should a subject move, a vessel that was intended to be in the tag condition will not be moved into a control condition and vice versa. The mask radius can give control over the trade-off between SNR efficiency and motion robustness, and can be tailored for each subject group.

The transverse gradients in the VEPCASL labeling pulse train used in this study are unipolar [13], i.e. for a given encoding function all have the same amplitude and direction, though this is not a requirement. The inversion efficiency curve that results after subtraction of a label from a control situation can be well represented by a sum of three Fourier coefficients [13]. In one or more aspects, our method implicitly assumes that the periodic labeling efficiency in VEPCASL is sinusoidal. However, the root mean squared difference between the sum of these coefficients and a perfect sinusoid is small (only 0.12), so errors resulting from this assumption are likely to be minimal. Note that a more precise representation of the encoding function applied during each VEPCASL cycle can be used in post processing, allowing the resulting images to be better decoded into vessel-specific maps.

Figure 3:
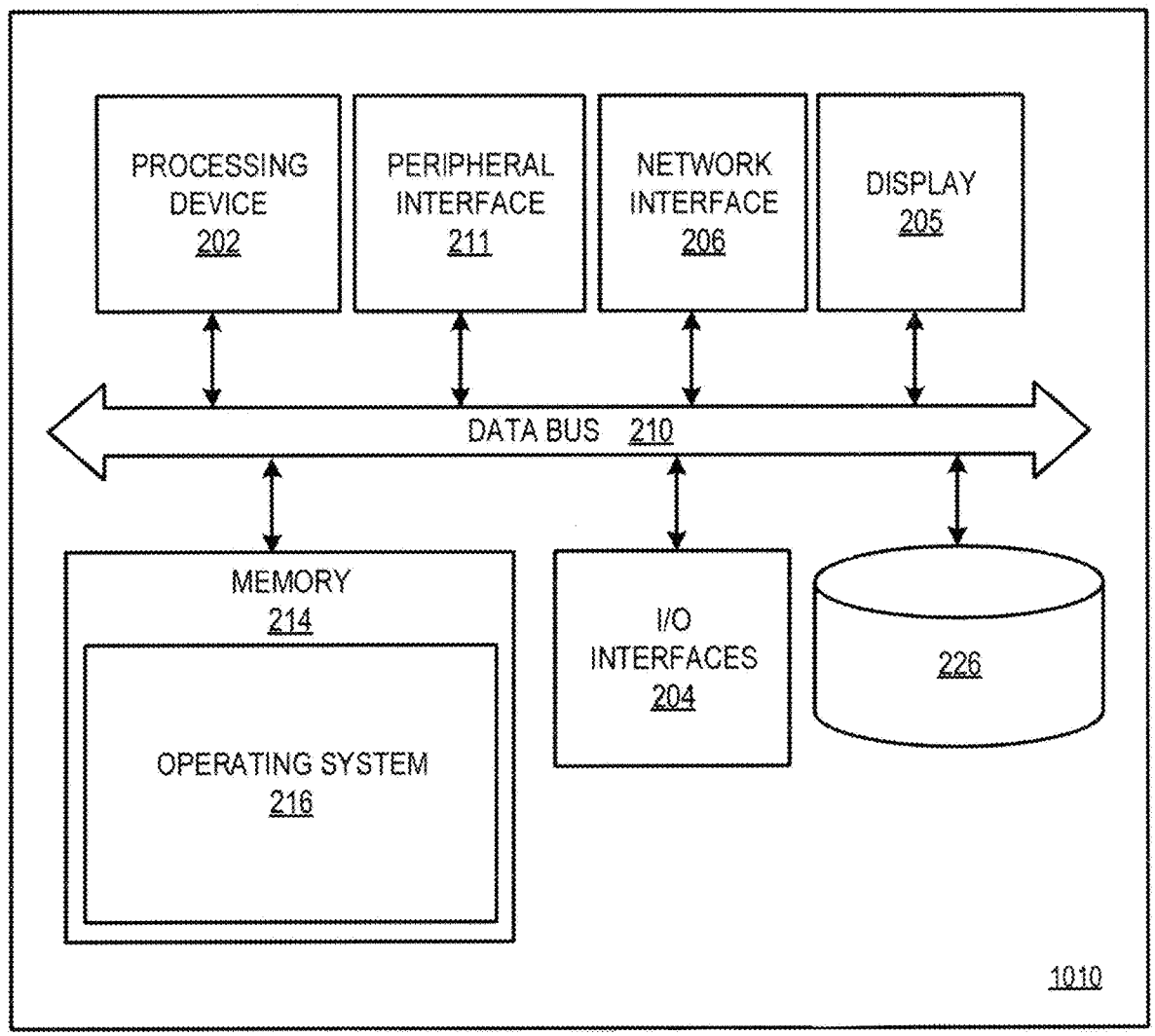
FIG. 3 is a schematic block diagram of an apparatus in which embodiments of the present systems and methods for off-resonance correction disclosed herein may be implemented.

Reference is now made to FIG. 3, which depicts an apparatus 1010 in which the present systems and methods described herein may be implemented, among others. The apparatus 1010 may be embodied in any one of a wide variety of wired and/or wireless computing devices, multi-processor computing device, and so forth. As shown in FIG. 3, the apparatus 1010 comprises memory 214, a processing device 202, one or more input/output interfaces 204, a network interface 206, a display 205, a peripheral interface 211, and mass storage 226, wherein each of these devices are connected across a local data bus 210. The apparatus 1010 may be coupled to one or more peripheral measurement devices (not shown) connected to the apparatus 1010 via the peripheral interface 211.

The processing device 202 may include any custom made or commercially available processor, a central processing unit (CPU) or an auxiliary processor among several processors associated with the apparatus 1010, a semiconductor based microprocessor (in the form of a microchip), a macroprocessor, one or more application specific integrated circuits (ASICs), a plurality of suitably configured digital logic gates, and other well-known electrical configurations comprising discrete elements both individually and in various combinations to coordinate the overall operation of the computing system.

The memory 214 can include any one of a combination of volatile memory elements (e.g., random-access memory (RAM, such as DRAM, and SRAM, etc.)) and nonvolatile memory elements (e.g., ROM, hard drive, tape, CDROM, etc.). The memory 214 typically comprises a native operating system 216, one or more native applications, emulation systems, or emulated applications for any of a variety of operating systems and/or emulated hardware platforms, emulated operating systems, etc. For example, the applications may include application specific software which may be configured to perform some or all of the systems and methods for quantification of arterial spin labeling dynamic angiography and perfusion described herein. In accordance with such embodiments, the application specific software is stored in memory 214 and executed by the processing device 202. One of ordinary skill in the art will appreciate that the memory 214 can, and typically will, comprise other components which have been omitted for purposes of brevity.

The one or more input/output interfaces 204 provide any number of interfaces for the input and output of data. For example, where the apparatus 1010 comprises a personal computer, these components may interface with one or more user input devices 204. The display 205 may comprise a computer monitor, a plasma screen for a PC, a liquid crystal display (LCD) on a hand held device, a touch screen or other display device.

In an embodiment of this disclosure, a non-transitory computer-readable medium stores programs for use by or in connection with an instruction execution system, apparatus, or device. More specific examples of a computer-readable medium may include by way of example and without limitation: a portable computer diskette, a random access memory (RAM), a read-only memory (ROM), an erasable programmable read-only memory (EPROM, EEPROM, or Flash memory), and a portable compact disc read-only memory (CDROM) (optical).

With further reference to FIG. 3, network interface device 206 comprises various components used to transmit and/or receive data over a network environment. For example, the network interface 206 may Include a device that can communicate with both inputs and outputs, for instance, a modulator/demodulator (e.g., a modem), wireless (e.g., radio frequency (RF)) transceiver, a telephonic interface, a bridge, a router, network card, etc.). The apparatus 1010 may communicate with one or more computing devices (not shown) via the network interface 206 over the network 118 (not shown). The apparatus 1010 may further comprise mass storage 226. The peripheral 211 interface supports various interfaces including, but not limited to IEEE-1394 High Performance Serial Bus (Firewire), USB, a serial connection, and a parallel connection.

The apparatus 1010 shown in FIG. 3 may be embodied, for example, as a magnetic resonance apparatus, which includes a processing module or logic for performing conditional data processing, and may be implemented either off-line or directly in a magnetic resonance apparatus. For such embodiments, the apparatus 1010 may be implemented as a multi-channel, multi-coil system with advanced parallel image processing capabilities, and direct implementation makes it possible to generate images, for example, immediate T1 maps, available for viewing immediately after image acquisition, thereby allowing re-acquisition on-the-spot if necessary. Examples of apparatus in which the present systems and methods may be implemented are described in U.S. Pat. Nos. 5,993,398 and 6,245,027 and Publication No. 2011/0181285, which are incorporated by reference as if fully set forth herein.

The method of FIG. 2 shows an example of functionality that can be implemented in the apparatus 1010 of FIG. 3. If embodied in software, each step shown in FIG. 2 may represent a module, segment, or portion of code that comprises program instructions to implement the specified logical function(s). The program instructions may be embodied in the form of source code that comprises machine code that comprises numerical instructions recognizable by a suitable execution system such as the processing device 202 (FIG. 3) in a computer system or other system. The machine code may be converted from the source code, etc. If embodied in hardware, each block may represent a circuit or a number of interconnected circuits to implement the specified logical function(s).

Although FIG. 2 shows a specific order of execution, it is understood that the order of execution can differ from that which is depicted. For example, the order of execution of two or more steps may be scrambled relative to the order shown. Also, two or more steps shown in succession in FIG. 2 may be executed concurrently or with partial concurrence. Further, in some embodiments, one or more of the steps shown in FIG. 2 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein that comprises software or code can be embodied in any non-transitory computer-readable medium for use by or in connection with an instruction execution system such as, for example, a processing device 202 in a computer system or other system. In this sense, each may comprise, for example, statements including instructions and declarations that can be fetched from the computer-readable medium and executed by the instruction execution system.

METHODS

The robustness of our ORC method was evaluated through simulations, a phantom scan and a scan healthy volunteers.

Our Off-Resonance Correction (ORC) Method

When considering four vessels, the encoding matrix described by Okell et al. [1] was used so that paired encodings were available. When considering more than four vessels, the columns of a Hadamard matrix were used as the vessel-encoding matrix. The calculations of the optimal encodings including correction for off-resonance were performed in MATLAB (MathWorks, Natick, Mass., USA). The calculation time for a set of encodings using a standard laptop was short: <2 s for four vessels and <3 s for nine vessels.

For all ORC calculations, the "image" of the vessels was zero-padded into a 1024×1024 matrix to give the most accurate spatial frequencies and phases without unnecessarily increasing the computation time. The expected maximum subject motion was set to 4 mm in all cases, as the predicted motion of healthy volunteers is low. This value results in a Fourier space mask that allows some higher spatial frequencies to be chosen. Consequently, it is possible to differentiate between vessels close together, as would be expected in blood vessel configurations above the circle of Willis.

Simulations

Prior to performing simulations, the inversion efficiency of the VEPCASL pulse train was simulated in MATLAB from the Bloch equations. Laminar flow and a blood velocity of 0.3 m·s$^{-1}$ were assumed and the inversion efficiency was adjusted to take this into account according to Dai et al. [14]. Encoding values were then drawn from this curve to give a more accurate representation of the encoding matrices. The SNR efficiency was averaged across all vessels to simplify comparison between the different simulation scenarios.

The encodings for a set of four vessels were simulated in MATLAB and their SNR efficiency compared for three cases:

1. No phase offset present it at the vessel locations
2. Phase offsets present, no ORC included in the encodings
3. Phase offsets present, ORC applied to the encodings.

The phase offsets used were taken from two field maps of a phantom in which linear and quadratic shim offsets had been applied. The phase offsets were gradually increased to test the method across twenty offsets ranging from −300 to 372 Hz.

Phantom Scan

A Eurospin test object 3 phantom, containing plastic rods used to represent the main brain feeding arteries in the neck, was scanned on a Siemens 3T TIM Verio system with a 12-channel head coil. The labeling parameters of Okell et al [1] were used, with a labeling duration of 400 ms and, following a post labeling delay of 16 ms, a single imaging slice (spoiled-gradient echo readout, flip angle=10°, voxel size=0.9×0.9×5 mm, TR=118.4 ms, TE=2.95 ms) placed across the labeling plane to image the encodings for the three scenarios tested in simulations. A large linear shim term was applied in the x direction (right to left) to generate a phase offset in the labeling plane. The phase offsets at the vessels needed to calculate the corrected encodings were taken from field maps of the labeling plane (voxel size=4.1×4.1×5 mm, TR=400 ms, TE1=5.19 ms, TE2=7.65 ms, acquisition time <1 min). A correction for 1D phase wrapping was applied to the phase values at the vessels to get the true offsets.

Subject Scan

PCASL and VEPCASL perfusion scans were performed with the labelling plane in the neck to provide perfusion data for the four main brain-feeding arteries, for the scenarios tested in simulations. Similarly to the phantom scans, to test the response of the correction to off-resonance, phase offsets were induced in the labelling plane by both shifting the automated shim adjustment volume higher in the brain and modifying the in-plane and through-plane shim currents. Scans where the shim volume and gradients were set automatically by the system were deemed to be those with no phase offsets present, as they are comparable to current (VE)PCASL studies. The shim settings were kept the same across all field map and perfusion data acquisitions for a given scenario. (VE)PCASL labeling and imaging parameters were as in Berry et al. [10]

Prior to all (VE)PCASL scans a three-dimensional multislab TOF angiography sequence was performed to allow selection of a labelling plane and localization of vessels (voxel size=0.8×0.8×1.3 mm). Additionally, field maps of the labelling plane and the imaging region were acquired during each scan. The resolution of the labelling plane field map was brought into line with the TOF scan to better localize the phase offsets at the vessels (voxel size=0.9× 0.9×2.0 mm, TR=200 ms, TE1=5.19 ms, TE2=6.19 ms, acquisition time=1 minute). The difference between the two echo times was adjusted to be the same as RF pulse spacing in the labelling train. Phase wrapping effects in the field map could then be ignored when determining phase offsets at the vessel locations.

PCASL scans of 40 measurements (acquisition time ~2'27 s) were performed on 6 subjects, 2 female, mean age 27±3 years. VEPCASL scans of 80 measurements (acquisition time ~4'45 s) were performed on 5 subjects, 1 female, mean age 27±3.5 years. PCASL and VEPCASL scans were acquired in an interleaved fashion in all of the scans, apart from one where only PCASL scans were performed. The data for one additional subject was excluded because all of the scans were severely motion corrupted. For each subject a field map of the imaged slices was acquired with the same resolution as the (VE)PCASL EPI readout (voxel size=3.4× 3.4×5.0, TR=200 ms, TE1=5.19 ms, TE2=7.65 ms, acquisition time=54 s) to make distortion correction of the EPI images possible prior to analysis.

Images were averaged across all repeats and image analysis was performed using a Bayesian maximum a posteriori (MAP) method [15] to separate out vessel-specific information. This MAP method considers subsets of the encoding matrix, hence it can deal with poorly conditioned matrices without significant loss of SNR. The correct assignment of vascular territories and the SNR in these territories was compared for the encodings with and without ORC.

RESULTS

Simulations

Figure 4:
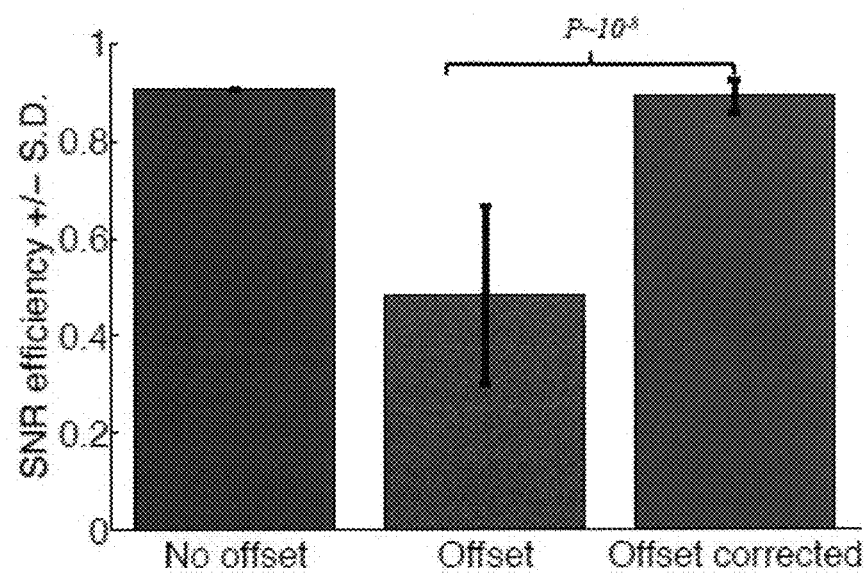
FIG. 4 depicts simulated mean SNR efficiencies of encodings calculated for three different scenarios: 1. No phase offset present at the vessel locations; 2. Phase offsets present, no off-resonance correction included in the encodings; 3. Phase offsets present, off-resonance correction applied to the encodings, across 20 different shim offsets.

The simulations demonstrate that corrected encodings result in a SNR efficiency similar to encodings when there is no offset and significantly more, according to a paired t-test, than when there is an offset present (FIG. 4).

Phantom Scan

Figures 5A, 5B, 5C, 5D:
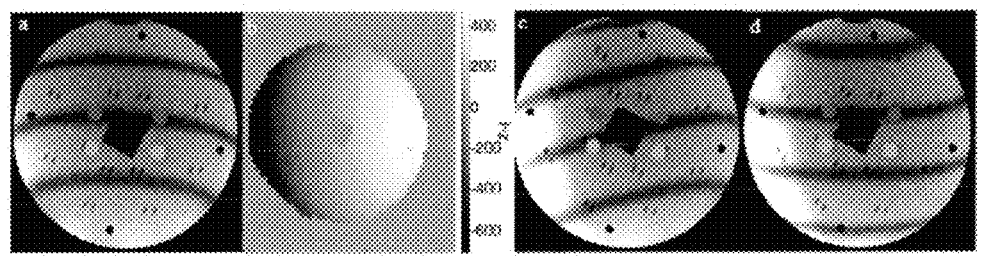
FIGS. 5a-5d depict images of a phantom in which the encodings in a labeling plane are imaged with and without a phase offset applied and with and without off-resonance correction included in the encodings. Blue dots=right/left internal carotid 'arteries', orange=right/left vertebrals. Dark stripes=labeled regions, pale=control.

FIGS. 5a-5d depict images of a phantom scan in which Anterior-Posterior (AP) encodings in a labeling plane are imaged with and without a phase offset applied and with and without off-resonance correction included in the encodings. FIG. 5a depicts (AP) encoding without any offset applied. Anterior arteries are labeled, posterior controlled. FIG. 5b depicts a field map showing a linear shim offset in the labeling plane. As can be seen, the encodings imaged in the phantom scan shift away from the vessel locations when an offset is present, demonstrating the effect off off-resonance in the labeling plane (FIG. 5c). The corrected encodings, however, clearly label the desired vessels (FIG. 5d).

Subject Scans

FIGS. 6a-6c show the perfusion signal in a single imaging slice of a representative subject following PCASL across the different scenarios tested. FIG. 6a depicts no offsets in the labelling plane. The images demonstrate the loss of signal in the brain (FIG. 6b) when there are phase offsets in the labelling plane (FIG. 6d) and the corresponding recovery of signal if the encodings are calculated to take these into account (FIG. 6c). Across the six subjects scanned the SNR of the no offset and corrected scenarios was significantly greater than the SNR from the offset scans according to a paired t-test (P=0.002 in both cases, FIG. 6e). The drop in SNR in the offset case represented a signal loss of ~32% versus the no offset case, whereas between the no offset and corrected scenarios there was only a 2% difference. Any signal loss leads to miscalculations in the cerebral blood flow, which is directly related to the perfusion signal.

FIGS. 7a-7c show the signal in the vascular territories of the main brain feeding arteries of a representative subject for a single imaging slice following VEPCASL across the different scenarios tested. FIG. 7a depicts no offsets in the labelling plane. The images demonstrate the miss-assignment of vascular territories during analysis (FIG. 7b) when there are phase offsets (FIG. 7d) in the labeling plane, and the restoration of the correct vascular territories if the encodings are calculated to take these into account (FIG. 7c). Across the five subjects scanned, as in the PCASL case, the SNR of the no offset and corrected scenarios was significantly greater than the SNR from the offset scans according to a paired t-test (P=0.004 and P=0.005, FIG. 7e).

DISCUSSION

Our ORC method can rapidly calculate SNR optimal vessel encodings, for any number and arrangement of arteries, that include a correction for phase offsets at the vessel locations. The method is computationally fast and is simple to integrate with any scanner operating system. Simulations, phantom and subject scans demonstrate the efficacy of including a phase offset correction in the calculation of optimized encodings for VEPCASL. Although it may be necessary to acquire a field map to perform this correction during a subject scan, and preferably any phase wrapping at the vessels of interest should be accounted for, the time needed to complete these processes is short (<1 min for a field map) and can be incorporated into a scan protocol. To prevent the need for phase unwrapping, the difference in echo time between the scans, for example two scans, used to calculate the field map can be made equal to the radio-frequency pulse gap in the PCASL labeling pulse train. The phase offsets from these field maps can thus be used directly in the ORC method of calculating encodings without the need for phase unwrapping. This method can also be used to correct for inhomogeneities in conventional PCASL scans, akin to previous studies [11, 12].

While we show encodings using manual intervention at the planning stage, somewhat complicating the acquisition process, our ORC method can include automation of the input of the vessel locations into the calculation of the encodings. This can simplify and speed up the planning process. One way this can be achieved can be to use a segmentation algorithm to find the vessel locations.

Our ORC method may be dependent to a certain extent on the choice of function used to weight the Fourier space. In the present study, a gradually varying function, with a maximum value of 0.5, was chosen so that if an encoding function with a high spatial frequency led to the most SNR-efficient encoding it was still likely to be selected, despite the weighting. However, where a number of spatial frequencies give a similar match to the desired ideal encoding, this weighting function encourages the selection of the lower spatial frequency. A linear weighting function was used in this study. However, other smooth, slowly varying weighting functions would yield similar results. It is also possible to adjust the Fourier space mask according to the predicted motion of a given subject population. This can make our ORC method robust to subject motion, although if the wavelength is limited to values larger than the vessel separations, the SNR efficiency of the encodings may drop.

Figure 8:
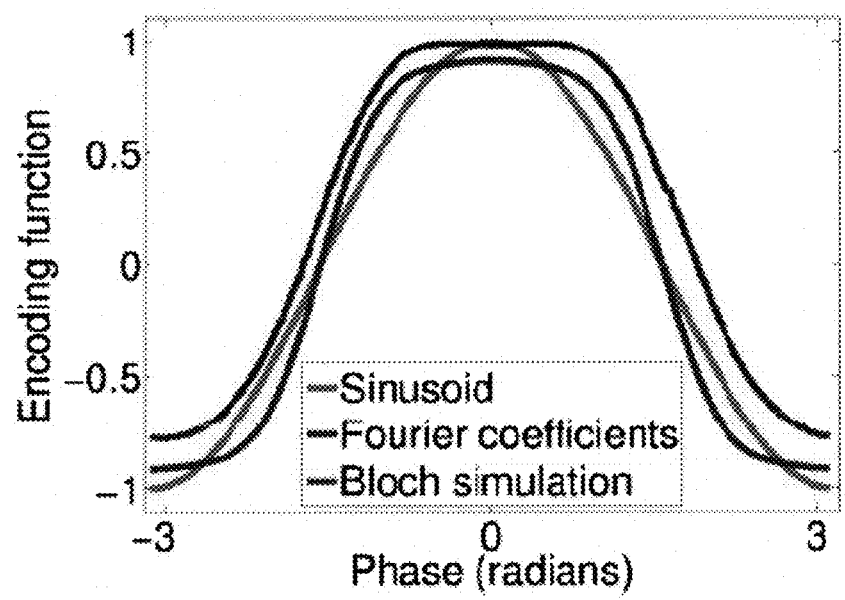
FIG. 8 depicts the inversion efficiency of the unipolar VEPCASL pulse train, simulated using the Bloch equations for a blood velocity of 0.3 m·s$^{-1}$, alongside the Fourier coefficients (scaled by 0.5) that best represent the subtraction of the labeled magnetization from the controlled magnetization for blood flow velocities between 0.05 and 0.4 m·s$^{-1}$ (18) and a sinusoid.

One potential limitation of this Fourier-based method is the implicit assumption that the encoding functions are sinusoids rather than a sum of Fourier coefficients. As such, it is an approximation, although both the sum of Fourier coefficients and the encoding function simulated using the Bloch equations are close to a sinusoid at the velocities typically found in the cerebral arteries (0.3-0.4 m s$^{-1}$ [16, 17], FIG. 8). It is also worth noting that the ideal encodings specify the labeling efficiency to be ±1 at each vessel location. Therefore, as long as the peaks/troughs of the encoding function are in the correct locations, the shape of the function in between is less critical.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

REFERENCES

1. Okell T W, Chappell M A, Woolrich M W, Gunther M, Feinberg D A, Jezzard P. Vessel-encoded dynamic magnetic resonance angiography using arterial spin labeling. Magn Reson Med 2010; 64:698-706.
2. Liebeskind D S. Collateral circulation. Stroke 2003; 34:2279-84.
3. van Laar P J, van der Grond J, Hendrikse J. Brain Perfusion Territory Imaging: Methods and Clinical Applications of Selective Arterial Spin-labeling MR Imaging. Radiology 2008; 246:354-364.
4. Bendszus M, Koltzenburg M, Burger R, Warmuth-Metz M, Hofmann E, Solymosi L. Silent embolism in diagnostic cerebral angiography and neurointerventional procedures: a prospective study. The Lancet 1999; 354:1594-1597.
5. Kaufmann T J, Kallmes D F. Diagnostic cerebral angiography: archaic and complication-prone or here to stay for another 80 years? AJR Am J Roentgenol 2008; 190:1435-7.
6. Wu W C, Fernandez-Seara M, Detre J A, Wehrli F W, Wang J. A theoretical and experimental investigation of the tagging efficiency of pseudocontinuous arterial spin labeling. Magn Reson Med 2007; 58:1020-7.
7. Okell T W, Chappell M A, Kelly M E, Jezzard P. Cerebral blood flow quantification using vessel-encoded arterial spin labeling. J Cereb Blood Flow Metab 2013; 33:1716-24.
8. Wong E C, Kansagra A. Mapping Middle Cerebral Artery Branch Territories with Vessel Encoded Pseudo-Continuous ASL: Sine/Cosine Tag Modulation and Data Clustering in Tagging Efficiency Space. In Proceedings of the 16th Annual Meeting of ISMRM, Toronto, 2008. p. 182.
9. Wong E C. Vessel-encoded arterial spin-labeling using pseudocontinuous tagging. Magn Reson Med 2007; 58:1086-1091.
10. Berry, E. S. K., Jezzard, P. and Okell, T. W. (2015), An Optimized Encoding Scheme for Planning Vessel-Encoded Pseudocontinuous Arterial Spin Labeling. Magn Reson Med, 74: 1248-1256. doi: 10.1002/mrm.25508
11. Jahanian H, Noll D C, Hernandez-Garcia L. B0 field inhomogeneity considerations in pseudo-continuous arterial spin labeling (pCASL): effects on tagging efficiency and correction strategy. NMR Biomed 2011; 24:1202-9.
12. Luh W M, Talagala S L, Li T Q, Bandettini P A. Pseudo-continuous arterial spin labeling at 7 T for human brain: estimation and correction for off-resonance effects using a Prescan. Magn Reson Med 2013; 69:402-10.
13. Wong E C, Guo J. Blind detection of vascular sources and territories using random vessel encoded arterial spin labeling. MAGMA 2012; 25:95-101.
14. Dai W Y, Garcia D, de Bazelaire C, Alsop D C. Continuous Flow-Driven Inversion for Arterial Spin Labeling Using Pulsed Radio Frequency and Gradient Fields. Magn Reson Med 2008; 60:1488-1497.
15. Chappell M A, Okell T W, Payne S J, Jezzard P, Woolrich M W. A fast analysis method for non-invasive imaging of blood flow in individual cerebral arteries using vessel-encoded arterial spin labelling angiography. Med Image Anal 2012; 16:831-839.
16. Aldo Ferrara L, Mancini M, Iannuzzi R, Marotta T, Gaeta I, Pasanisi F, Postiglione A, Guida L. Carotid Diameter and Blond Flow Velocities in Cerebral Circulation in Hypertensive Patients. Stroke 1995; 26:418-421.
17. Bammer R, Hope T A, Aksoy M, Alley M T. Time-resolved 3D quantitative flow MRI of the major intracranial vessels: initial experience and comparative evaluation at 1.5 T and 3.0 T in combination with parallel imaging. Magn Reson Med 2007; 57:127-40.

What is claimed:

1. A method for off-resonance correction prior to an acquisition of arterial spin labeling (ASL) data, comprising:
   A. Providing a medical imaging device;
   B. Positioning a subject in association with the medical imaging device;
   C. Acquiring location information of one or more blood vessels of interest in the subject and a phase offset induced by off-resonance at a location of each of the one or more blood vessels;
   D. Determining a set of off resonance corrected encodings to apply to a labeling plane to encode the one or more blood vessels of interest whilst accounting for the acquired phase offset at each of the one or more blood vessel locations for which information is acquired, wherein the set of off resonance corrected encodings is determined by;

constructing a matrix with values of the one or more blood vessels at positions corresponding to their location, including subtraction of the acquired phase offset at each position corresponding to the location of each of the one or more blood vessels;

up-weighting lower spatial frequencies in a Fourier space or transform domain of the constructed matrix; and finding a maximum intensity point in the up-weighted Fourier space or transform domain for determining the set of off-resonance corrected encodings; and E. Acquiring arterial spin labeling (ASL) data, which includes the one or more blood vessels of interest in the subject, using the determined set of off-resonance corrected encodings and using the medical imaging device.

2. The method of claim 1, wherein the arterial spin labeling (ASL) data acquired includes pseudo-continuous arterial spin labeling (PCASL) or vessel-encoded pseudo-continuous arterial spin labeling (VEPCASL) data or both.

3. The method of claim 1, wherein the step of acquiring information about the location of the one or more blood vessels of interest and the phase offset at the location of each of the one or more blood vessels includes constructing the matrix and placing the one or more blood vessels in the matrix at positions corresponding to their physical Cartesian coordinates within the labeling plane.

4. The method of claim 1, further including a step of zero-padding the matrix.

5. The method of claim 1, wherein the step of up-weighting the lower spatial frequencies includes masking spatial frequencies within the Fourier space or transform domain, or wherein before the maximum intensity point is found, an absolute value of the Fourier space or transform domain is taken and normalized to its maximum value and then the up-weighting is done, or both.

6. The method of claim 1, wherein the set of off-resonance corrected encodings is calculated for more than three vessels.

7. The method of claim 1, wherein the step of acquiring information about the location of the one or more blood vessels of interest and the phase offset at the location of each of the one or more blood vessels includes constructing the matrix and the step is repeated for each cycle of the set of off resonance corrected encodings.

8. The method of claim 1, wherein the data includes perfusion data or static/dynamic angiography data.

9. The method of claim 1, wherein the step of acquiring information about the location of the one or more blood vessels of interest and phase offset at the location of each of the one or more blood vessels involves a field map of the labeling plane, includes input of the one or more blood vessel locations, includes constructing the matrix of the one or more blood vessels, or two or more thereof.

10. The method of claim 9, wherein the phase offset subtracted at each position is calculated via the field map.

11. The method of claim 1, wherein determining the set of off-resonance corrected encodings further comprises:

zero-padding the matrix; taking Fourier transform of the zero-padded matrix to create the Fourier space; up-weighting and masking the Fourier space; and determining the maximum intensity point in the up-weighted Fourier space for determining the set of off-resonance corrected encodings.

12. The method of claim 11, further comprising zero-padding the matrix after the step of subtracting the acquired phase offset.

13. A system for off-resonance correction prior to an acquisition of arterial spin labeling data comprising: at least one medical imaging device configured for positioning a subject in association with the medical imaging device; at least one computing device in data communication with the medical imaging device; and an application executable in the at least one computing device, the application comprising logic that:

A. Acquires location information of one or more blood vessels of interest in the subject and a phase offset induced by off-resonance at a location of each of the one or more blood vessels;

B. Determines a set of encodings to apply to a labeling plane to encode the one or more blood vessels of interest whilst accounting for the acquired phase off set at each of the one or more blood vessel locations for which information is acquired, wherein the set of encodings is determined by;

constructing a matrix with values of the one or more blood vessels at positions in the matrix corresponding to their location, including subtraction of the acquired phase offsets at each position corresponding to the location of each of the one or more blood vessels;

up-weighting lower spatial frequencies in a Fourier space or transform domain of the constructed matrix; and finding a maximum intensity point in the up-weighted Fourier space or transform domain for determining the set of encodings; and C. Acquires arterial spin labeling data, which includes the one or more blood vessels of interest in the subject, using the determined set of encodings and using the medical imaging device.

14. The system of claim 13, wherein the logic that acquires information about the location of the one or more blood vessels of interest and the phase offset at the location of each of the one or more blood vessels includes constructing the matrix and placing the one or more blood vessels in the matrix at positions corresponding to their physical Cartesian coordinates within the labeling plane.

15. The system of claim 13, wherein the logic that up-weights the lower spatial frequencies includes masking spatial frequencies within the Fourier space or transform domain, or wherein before the maximum intensity point is found, takes an absolute value of the Fourier space or transform domain and normalizes it to its maximum value, or both.

16. The system of claim 13, wherein the logic that acquires information about the location of the one or more blood vessels of interest and the phase offset at the location of each of the one or more blood vessels involves a field map of the labeling plane, includes input of the one or more blood vessel locations, includes constructing the matrix of the one or more blood vessels, or two or more thereof.

17. The system of claim 16, wherein the phase offset subtracted at each position is calculated via the field map.

18. A non-transitory computer-readable medium employing a program executable in at least one computing device, comprising code that:

A. Acquires location information of one or more blood vessels of interest in a subject and a phase offset induced by off-resonance at a location of each of the one or more blood vessels of interest from a medical imaging device configured for positioning the subject in association with the medical imaging device;

B. Determines a set of off-resonance corrected encodings to apply to a labeling plane to encode the one or more blood vessels of interest whilst accounting for the acquired phase offset at each of the one or more blood vessel locations for which information is acquired, wherein the set of off-resonance corrected encodings is determined by;

constructing an image matrix with values of the one or more blood vessels at positions within the image matrix corresponding to their location, including subtraction of the acquired phase offset at each position corresponding to the location of each of the one or more blood vessels;

up-weighting lower spatial frequencies in a Fourier space or transform domain of the constructed image matrix; and finding a maximum intensity point in the up-weighted Fourier space or transform domain for determining the set of off-resonance corrected encodings; and C. Acquires arterial spin labeling data, which includes the one or more blood vessels of interest in the subject, using the determined set of off-resonance corrected encodings and using the medical imaging device.

19. The non-transitory computer-readable medium of claim 18, wherein the code that acquires information about the location of the one or more blood vessels of interest and the phase offset at the location of each of the one or more blood vessels involves a field map of the labeling plane, includes input of the one or more blood vessel locations, includes constructing the image matrix of the one or more blood vessels, or two or more thereof.

20. The non-transitory computer-readable medium of claim 18, wherein the code constructs the image matrix and places the one or more blood vessels in the image matrix at positions corresponding to their physical Cartesian coordinates within the labeling plane.

21. The non-transitory computer-readable medium of claim 18, wherein the code masks spatial frequencies within the Fourier space or transform domain, or wherein before the maximum intensity point is found, takes an absolute value of the Fourier space or transform domain and normalizes it to its maximum value, or both.

* * * * *